United States Patent [19]

Metal

[11] 4,434,369
[45] Feb. 28, 1984

[54] RADIOGRAPHIC CAMERA

[75] Inventor: Israel Metal, New York, N.Y.

[73] Assignee: Raytheon Company, Lexington, Mass.

[21] Appl. No.: 222,182

[22] Filed: Jan. 2, 1981

[51] Int. Cl.³ .............................................. G01T 1/20
[52] U.S. Cl. .............................. 250/363 S; 250/366; 250/369
[58] Field of Search ................... 250/363 S, 366, 369; 364/414, 515, 723, 853

[56] References Cited

U.S. PATENT DOCUMENTS 4,060,730  11/1977  Zioni et al. ........................ 250/369

Primary Examiner—Alfred E. Smith
Assistant Examiner—Carolyn E. Fields
Attorney, Agent, or Firm—Richard M. Sharkansky; Joseph D. Pannone

[57] ABSTRACT

A radiographic camera is provided having a scintillator and a plurality of photodetectors positioned to face the scintillator for providing position electrical signals. The photodetectors are disposed at different, progressively increasing, predetermined distances from a reference point to a distal point adjacent the outer periphery of a nominal field of view of the camera. The position electrical signal provided by each one of the plurality of photodetectors has an amplitude related to the distance between such one of the photodetectors and the point of impingement of radiation on the scintillator. Circuitry, responsive to a plurality of the position electrical signals, is provided for producing an extrapolated correction electrical signal, such correction electrical signal having an amplitude representative of the distance between the point of an impingement of radiation on the scintillator and a point beyond the distal point and outside of the nominal field of view of the camera. Additional circuitry, responsive to the position electrical signals and the correction electrical signal is provided for producing a pair of electrical signals representing the location of the impingement of the radiation on the scintillator relative to a reference point. With such arrangement, the nominal field of view of the camera is extended.

4 Claims, 6 Drawing Figures

RADIOGRAPHIC CAMERA

BACKGROUND OF THE INVENTION

This invention relates generally to radiation imaging systems and more particularly to imaging systems having extended fields of view.

As is known in the art, radiation imaging systems have been used to diagnose tumors and other diseased tissues. Typically, small amounts of radio isotopes, after being administered to a patient, concentrate differently in the diseased and healthy tissues. The different concentrations of radiation, usually gamma rays, emitted by the healthy and diseased tissues are thus distinct and can be detected. Further, such imaging systems have been used to form images of various human organs. For cardiac imaging and dynamic function studies it is generally desirable that the camera be relatively small, relatively transportable, and have high resolution and uniformity with an adequate field of view size.

As is also known, the cameras used in providing an image of a radio active source are frequently comprised of a scintillator crystal and a collimator for guiding radiant energy from the source to the scintillator crystal. An array of photomultipliers is positioned on the opposite side of the scintillator crystal for receiving flashes of light emitted by the crystal in response to the incident radiant energy. Typically, the measure of light energy recovered by each photomultiplier is obtained by integrating circuits coupled to each of the photomultipliers, the relative magnitudes of these energies serving to indicate the location of each of the light flashes on the crystal. The signals produced by the integrators are combined in an appropriate weighting circuit to provide points on display, such as a cathode ray tube display, which correspond to the points of illumination upon the scintillated crystal. A circuit having an electronic window or gate, frequently referred to as a pulse height analyzer, is utilized in coupling the signals from the photomultipliers to the display to ensure that only signals having an energy within a prescribed range of energies are coupled to the display. Since, as noted above, for cardiac imaging and diagnostic function studies it is generally desirable that the camera be relatively small, readily transportable and have a high resolution and uniformity, it is desirable to provide a camera having a given number of photomultipliers with a maximum possible field of view.

SUMMARY OF THE INVENTION

In accordance with the invention a radiographic camera is provided having a scintillator, a plurality of photodetectors positioned to face the scintillator for providing, within a nominal field of view of the camera, position electrical signals, the position electrical signal provided by each one of the plurality of photodetector means having an amplitude related to the distance between the photodetector and the point of an impingement of radiation on said such scintillator. Means, responsive to a plurality of the position electrical signals, are provided for producing a correction electrical signal, such correction electrical signal having an amplitude representative of the distance between the point of impingement of radiation on the scintillator and a point beyond the nominal field of view of the camera. Means, responsive to the position electrical signal and the correction electrical signal, are provided for producing a pair of electrical signals representing the location of the impingement of the radiation on the scintillator relative to a reference point.

In a preferred embodiment of the invention the photodetector means includes an array of photodetectors arranged in a plurality of sets of rows, the photodetectors in each of such sets of rows being at successively increasing distances from the central region of the scintillator. Means coupled to each one of the rows of the photodetectors provide electrical signals representative of the distance from the point of impingement of the radiation on the scintillator and the distance from such one of the rows on the photodetectors. Such electrical signals are combined to provide an extrapolated electrical signal representative of the distance from the point of impingement to a phantom row of photodetectors disposed beyond the distal one of the rows of photodetectors in the set thereof. The extrapolated electrical signal represents the electrical signal which would have been produced if the phantom row of photodetectors were a row of actual photodetectors in such set of photodetectors. The extrapolated signal, together with the electrical signals produced by the rows of photodetectors, are combined to provide an indication of the position of the impingement of radiation on the scintillator. With such arrangement, the extrapolated electrical signals are able to increase the field of view of the camera from that obtained with processing merely the electrical signals produced by the rows of photodetectors.

BRIEF DESCRIPTION OF THE DRAWINGS

The aforementioned aspects and other features of the invention are explained in the following description taken together in connection with the accompanying drawings, wherein.

DESCRIPTION OF THE PREFERRED EMBODIMENT

Figure 1:
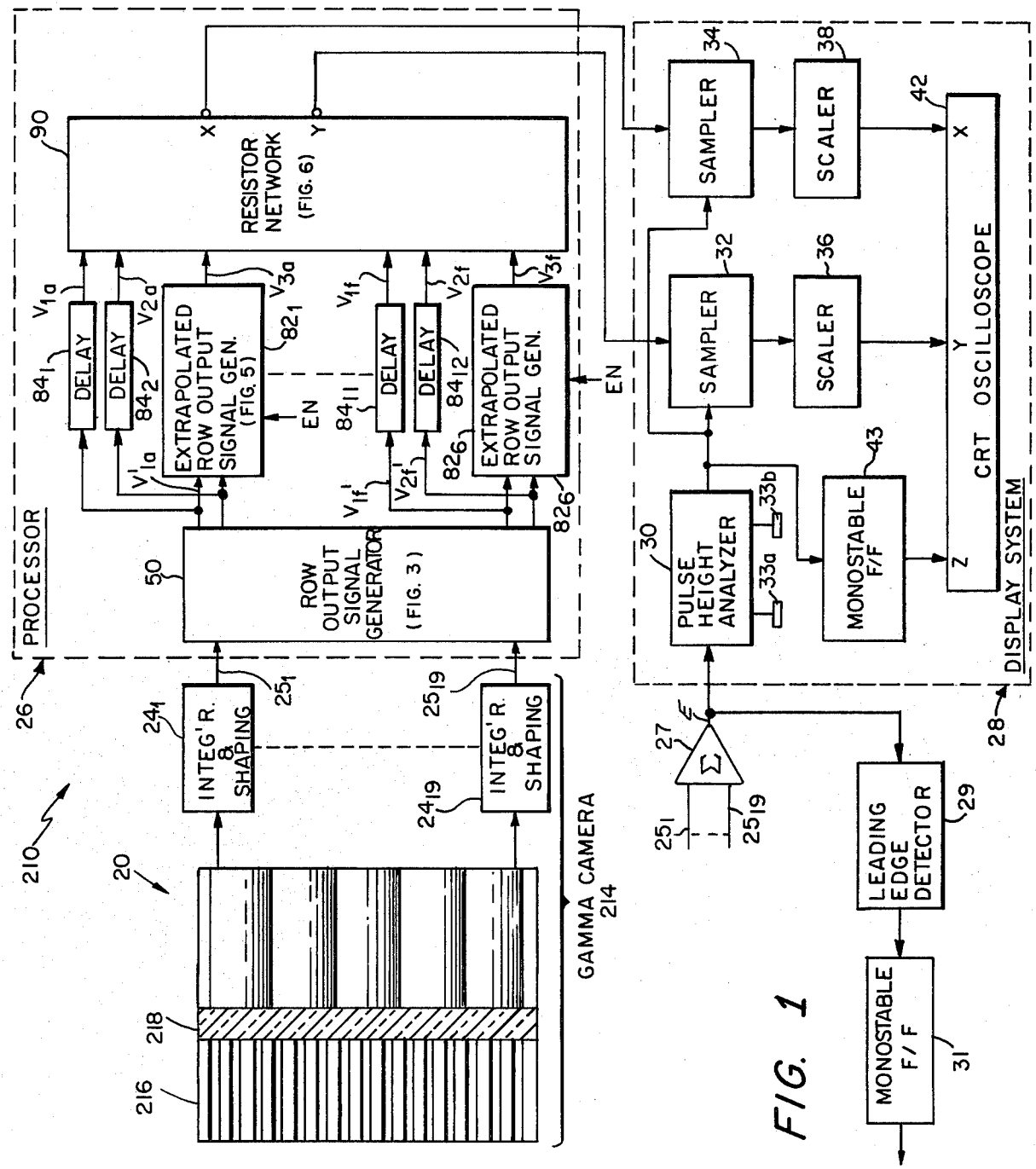
FIG. 1 is a block diagram of a radiographic camera system according to the invention.
Figure 2:
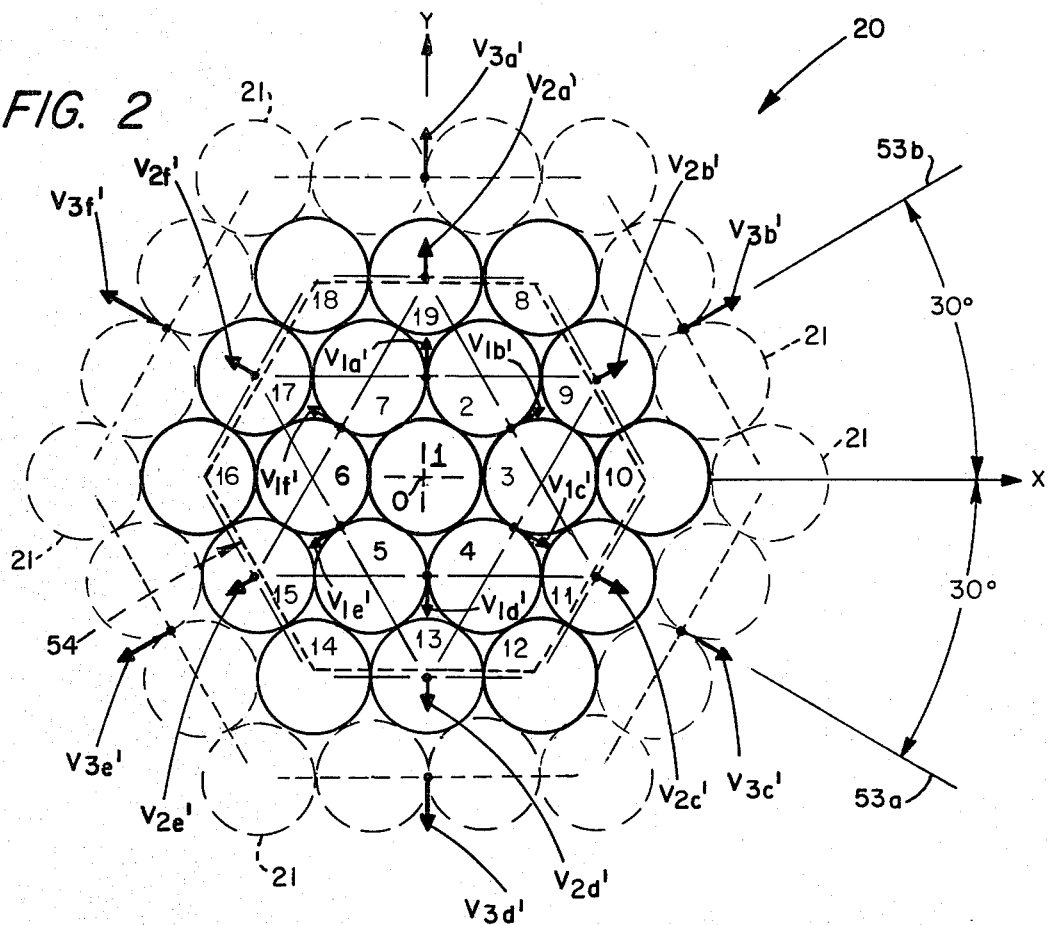
FIG. 2 is a diagram showing the arrangement of photodetectors used in the system of FIG. 1.

Referring now to FIG. 1, a block diagram of a radiographic system 210 is shown. A radiographic subject 212 such as a radioactive thyroid or heart is shown positioned in front of a gamma camera 214, such camera 214 being of any conventional design and including a collimator 216, a scintillator crystal 218 of a material such as sodium iodide which emits light in response to radiant energy from the subject 212, a set of, here ninteen, photomultiplier tubes 20 which face the scintillator crystal 218. The photomultipliers 20 are arranged in a hexagonal array as shown in FIG. 2. The array is centered about a reference point O as shown. The output of each one of the nineteen photomultiplier tubes 20 is coupled to a corresponding one of a plurality of integrator and shaping circuits $24_1$-$24_{19}$ of any conventional design for forming a single electrical pulse from the one of the photomultiplier tubes 20 coupled thereto in response to a flash of light emanating from the scintillator crystal 218, such flash of light being produced by such scintillator crystal 218 in response to a single radiation event or a single impingement of radiation on the scintillator crystal 18. Such a camera 214 has been described in U.S. Pat. No. 3,914,611 issued Oct. 21, 1975 and U.S. Pat. No. 3,980,886 issued Sept. 14, 1976, inventor Carl J. Stout. The pulses produced at the outputs of the integrator and shaping circuits $24_1$-$24_{19}$ are fed to a summing network 27 and a processor 26, the details of which will be described hereinafter. Suffice it to say here, however, that in response to each single impingement of the scintillator crystal 218 by a gamma ray photon, a pulse is produced by each one of the integrator and shaping circuits $24_1$-$24_{19}$, the relative levels of such pulses being related to the location of the impact of the gamma ray photon on the scintillator crystal 218 relative to the photodetectors coupled thereto. The processor 26, in response to the pulses provided by the integrator and shaping circuits $24_1$-$24_{19}$ on lines $25_1$-$25_{19}$, produces signals representing the X and Y coordinates of the location of the impact of a gamma ray photon upon the scintillator crystal 218, such X and Y coordinates being centered at the reference point 0. The signals produced by the integrator and shaping circuits $24_1$-$24_{19}$ on lines $25_1$-$25_9$ are also fed to a summing network 27 which produces an E signal representative of the magnitude of the energy content of the radiation received by the camera 214 in response to the radiation event (i.e., the total energy received by the ninteen photomultiplier tubes 20). The X and Y produced by the processor 26 and the E signal produced by summing network 27 are fed to a display system 28 comprising a pulse height analyzer 30, a pair of samplers 32, 34, a pair of scalers 36, 38, and a cathode ray tube (CRT) oscilloscope 42. The pulse height analyzer 30 passes pulses through samplers 32, 34 having amplitudes greater than a minimum threshold value and smaller than a maximum threshold level, these levels being set by the knobs 33a, 33b. The sampled X, Y pulse signals are, after scaling by scalers 36, 38, passed from the processor for presentation on the oscilloscope 42. The Z axis of the oscilloscope 42 is triggered by passing the pulse produced by the pulse height analyzer 30 through a monostable multivibrator (or flip/flop) 43. The E signal is fed to line EN via a leading edge detector 29 and monostable F/F 31 to produce a pulse on line EN a short time after the leading edge of, and during a portion of the time of, the pulse produced by the networks $24_1$-$24_{19}$.

Referring briefly to FIG. 2, the nineteen photomultiplier tubes 20 are shown to be arranged in a hexagonal array, with individual ones of the photomultiplier tubes 20 being numbered to identify its location in the array. The central photomultiplier tube is numbered 1, the photomultiplier tubes in the inner inner hexagon are numbered 2 through 7 and the photomultiplier tubes of the outer hexagon are numbered 8 through 19.

Referring again also to FIG. 1, the scintillator crystal 218 is of the form of a crystal of a material which emits light in response to excitation from high energy radiation, such a material being, for example, sodium iodide with thallium doping. The scintillator crystal 218 is supported in relation to the photomultiplier tubes 20 by means of the housing (not shown). A collimator 216 having parallel passageways for conducting high energy photons to the scintillator is positioned in front of the scintillator crystal 218 by means of the housing and oriented in the direction of the source of high energy radiation. High energy photons emitted from the source 212 in the direction of the axis of the collimator 216 pass through passages to illuminate the scintillator 216 in a pattern corresponding to the form of the source 212. Photons incident on the collimator 216 in a nonaxial direction are substantially absorbed in the material, preferably lead, from which the collimator is fabricated as described in the U.S. patents referred to above.

Figure 3:
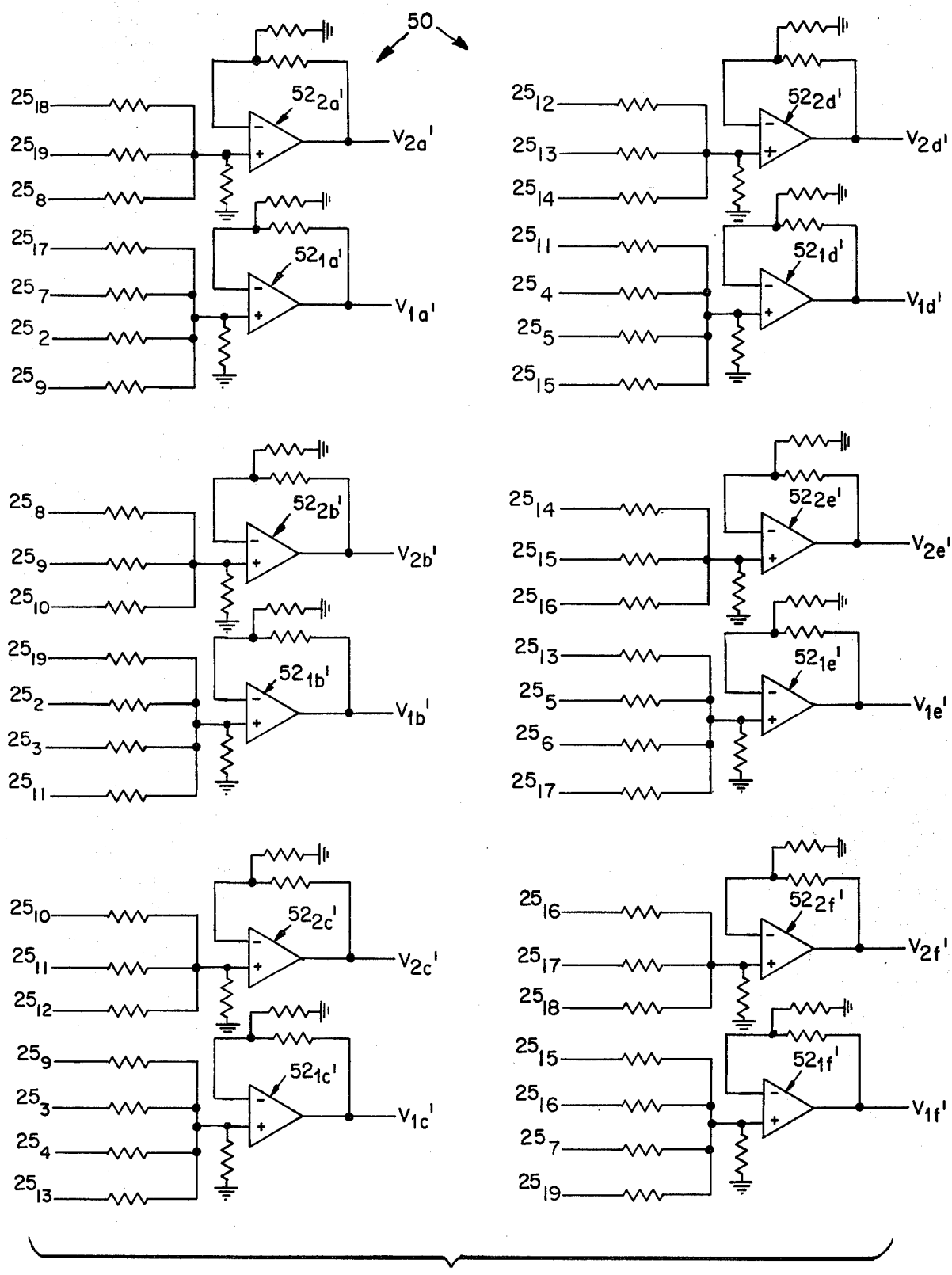
FIG. 3 is a schematic diagram of a row output signal generator used in the system of FIG. 1.
Figure 4:
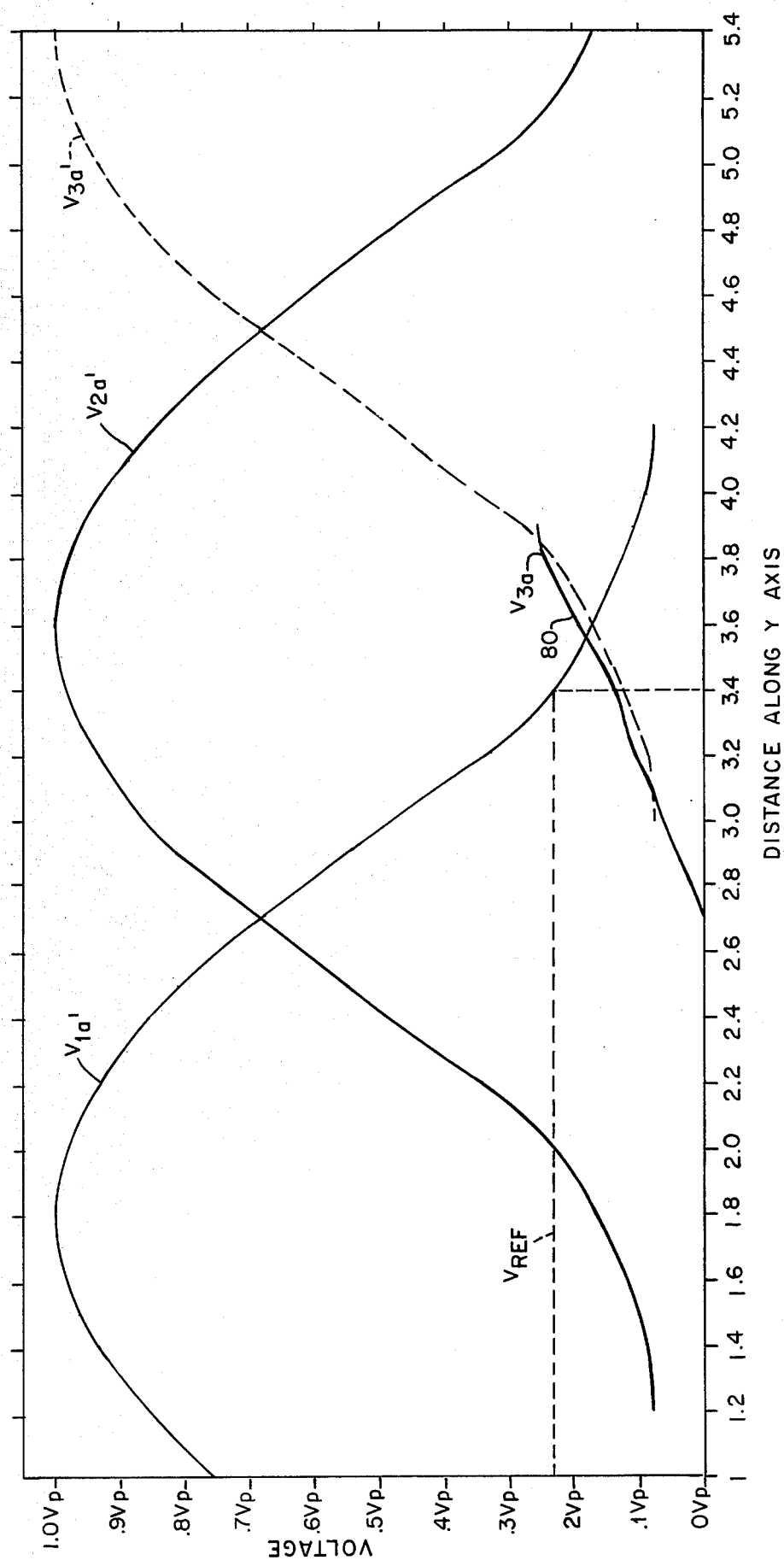
FIG. 4 is a graph showing the relationship between a pair of output voltages produced by the row output signal generator for a pair of adjacent rows of photodetectors and an extrapolated voltage produced in accordance with such pair of output voltages to represent the output voltage which would have been produced from a third row of photodetectors had such third row of photodetectors been disposed adjacent a distal one of the pair of rows of photodetectors.

As shown in FIG. 2, a reference frame having an X coordinate axis and a Y coordinate axis may be positioned anywhere upon the array of photomultiplier tubes 20, but is conventionally centered upon the array of photomultiplier tubes 20 such that the Y axis passes through photomultiplier tubes numbered 19, 1 and 13, while the X axis passes through the photomultiplier tubes numbered 10, 3, 1, 6 and 16. The outputs of the photomultiplier tubes 20 numbered 1 to 19 are fed to integrator and shaping circuits $24_1$-$24_{19}$ (FIG. 1), respectively as noted above. The outputs of integrator and shaping circuits $24_1$-$24_{19}$ are fed to a row output signal generator 50 (FIG. 1) (the details of which are shown in FIG. 3) via lines $25_1$-$25_{19}$, respectively. Referring again to FIG. 2, it is noted that the array of photomultiplier tubes 20 is here considered as being disposed in six outer rows and six inner rows. The photomultiplier tubes 18, 19 and 8 form a first one of the six outer rows, photomultiplier tubes, 8, 9 and 10 form a second one of the six outer rows, photomultiplier tubes 10, 11 and 12 form a third one of the six outer rows, photomultiplier tubes 12, 13 and 14 form a fourth one of the six outer rows, photomultiplier tubes 14, 15 and 16 form a fifth one of the six outer rows and photomultiplier tubes 16, 17 and 18 form the sixth one of the six outer rows. The six inner rows of photomultiplier tubes are formed as follows: Photomultiplier tubes 17, 7, 2 and 9 form the first one of the six inner rows; photomultiplier tubes 19, 2, 3, and 11 form the second one of the six inner rows; photomultiplier tubes 9, 3, 4 and 13 form a third one of the six inner rows; photomultiplier tubes 11, 4, 5 and 15 form a fourth one of the six inner rows; photomultiplier tubes 13, 6, 5 and 17 form a fifth one of the six inner rows; and photomultiplier tubes 15, 6, 7 and 19 form the sixth one of the six inner rows. The outputs of the photomultiplier tubes 20 in each one of these twelve rows are combined together in photodetector row signal output generator 50 to form twelve composite row signals. Thus, the outputs of photomultiplier tubes 18, 19 and 8 are passed through integrator and shaping circuits $24_{18}$, $24_{19}$, $24_8$, respectively and are summed together in a summing amplifier $52_{2a'}$ (FIG. 3) to produce an output voltage $V_{2a'}$ as shown in FIG. 3. Likewise, the outputs of photomultiplier tubes 17, 7, 2 and 9 are summed together in summing amplifier $52_{1a'}$ to provide an output $V_{1a'}$. Thus, the voltage $V_{2b'}$ is produced at the output of summing amplifier $52_{2b'}$ and is the sum of the voltages of photomultiplier tubes 8, 9 and 10, while the voltage $V_{1b'}$ is the sum of the voltages produced at the output of summing amplifier $52_{1b'}$ in response to the outputs of photomultiplier tubes 19, 2, 3 and 11. The remaining voltages $V_{2c'}$, $V_{1c'}$, $V_{2d'}$, $V_{1d'}$, $V_{2e'}$, $V_{1e'}$, $V_{2f}$ and $V_{1f}$ are formed at the outputs of summing amplifiers $52_{2c'}$, $52_{1c'}$, $52_{2d'}$, $52_{1d'}$, $52_{2e'}$, $52_{1e'}$ $52_{2f}$ and $52_{1f}$, respectively, as shown in accordance with the schematic in FIG. 3. The voltages $V_{1a'}$, $V_{2a'}$ to $V_{1f}$, $V_{2f}$ may therefore be represented as vectors and such vectors are shown diagrammatically in FIG. 2. It is noted that while the vectors having subscripts a and d are aligned with the Y axis, the vectors having subscripts b, c, e and f are aligned along axes 53a, 53b disposed at 30° with respect to the X axis. It is also noted that the nineteen photomultiplier tubes 1–19 disposed as shown in FIG. 2 are able to provide an image of the subject 212 (FIG. 1) within a hexagonal shaped nominal field of view of the camera, such nominal field of view being designated by the dotted line 54 in FIG. 2. In particular, the location of each impact of a gamma ray photon on the scintillator crystal 22 (FIG. 1) relative to the reference point 0 may be determined by processing the voltages $V_{1a}$, $V_{2a}$ to $V_{1f}$, $V_{2f}$ to provide an X and Y output representative of the positon of such impact relative to the coordinate system shown in FIG. 2. It is noted, however, that the nominal field of view of the camera is here extended by extrapolating the voltages produced by adjacent rows of photodetector tubes 20 to produce the output voltages which would have been produced had additional rows of phantom photodetector tubes 21 been included in the array, such phantom photodetector rows being shown in phantom (i.e., as dotted circles). That is, referring to FIG. 4, the voltage $V_{1a'}$ and $V_{2a'}$ as a function of the position of the impact of radiation along the Y axis is shown. A theoretical voltage $V_{3a'}$, as shown in FIG. 4, is here constructed from a measurement of the voltage $V'_{1a}$ and $V'_{2a}$ at any distance along the Y axis. An approximation to this theoretical voltage $V_{3a'}$, i.e. a voltage $V_{3a}$, is shown in FIG. 4 by the curve 80. Such approximation to the theoretical voltage $V_{3a'}$ is here represented as:

$$V_{3a}=0; \; V_{1a'}>V_{2a'}$$

$$V_{3a}=K_a(V_{2a'}-V_{1a'}); \; V_{1a'}>V_{ref} \text{ and } V_{2a'}>V_{1a'}$$

$$V_{3a}=(K_bV_{2a'}-K_cV_{1a'}+V_0); \; V_{1a'}<V_{ref} \text{ and } V_{2a'}>V_{1a'}$$

where
$K_a=0.18$
$K_b=0$
$K_c=1.00$
$V_0=.365V_p$
$V_{ref}=0.23V_p$
$V_p$=peak output voltage of a row of the photodetector tubes as shown in FIG. 4.

Referring to FIG. 1, a voltage approximating the theoretical voltage $V_{3a'}$ (i.e. the voltage $V_{3a}$) is produced by extrapolated row output signal generator $82_1$, the details of which will be described in connection with FIG. 5. Likewise, extrapolated signals $V_{3b}$ to $V_{3f}$ are produced in response to voltages $V_{1b'}$, $V_{2b'}$ through $V_{3f'}$, $V_{2f}$, respectively, by extrapolated row output signal generators $82_2$ through $82_6$, respectively. That is, the voltages of each pair of adjacent, parallel rows of photodetectors (i.e., $V_{1b'}$, $V_{2b'}$ through $V_{1f}$, $V_{2f}$) produce an extrapolated voltage $V_{3b'}$ through $V_{3f}$ so that extrapolated voltages $V_{3b'}$ through $V_{3f}$, respectively, are produced by the extrapolation row signal output generators $82_2$–$82_6$, respectively, such extrapolated voltages $V_{3a'}$ through $V_{3f}$ being represented by vectors in FIG. 2. The voltages $V_{1a'}$, $V_{2a'}$ through $V_{1f}$, $V_{2f}$ are passed through delay networks $84_1$–$84_{12}$, such delay networks $84_1$–$84_{12}$ being provided to compensate for the delay in computing the extrapolated voltages $V_{3a}$–$V_{3f}$. The signals produced by the delay networks $84_1$–$84_{12}$ (i.e., $V_{1a}$–$V_{2f}$), together with the extrapolated voltages $V_{3a}$ through $V_{3f}$ are fed to a resistor network 90, details of which are shown in FIG. 6. The resistor network 90 combines such voltages $V_{1a}$ through $V_{3f}$ to produce the X and Y position signals for the display system 28. Also fed to generators $82_1$–$82_6$ is line EN, as shown.

Figure 5:
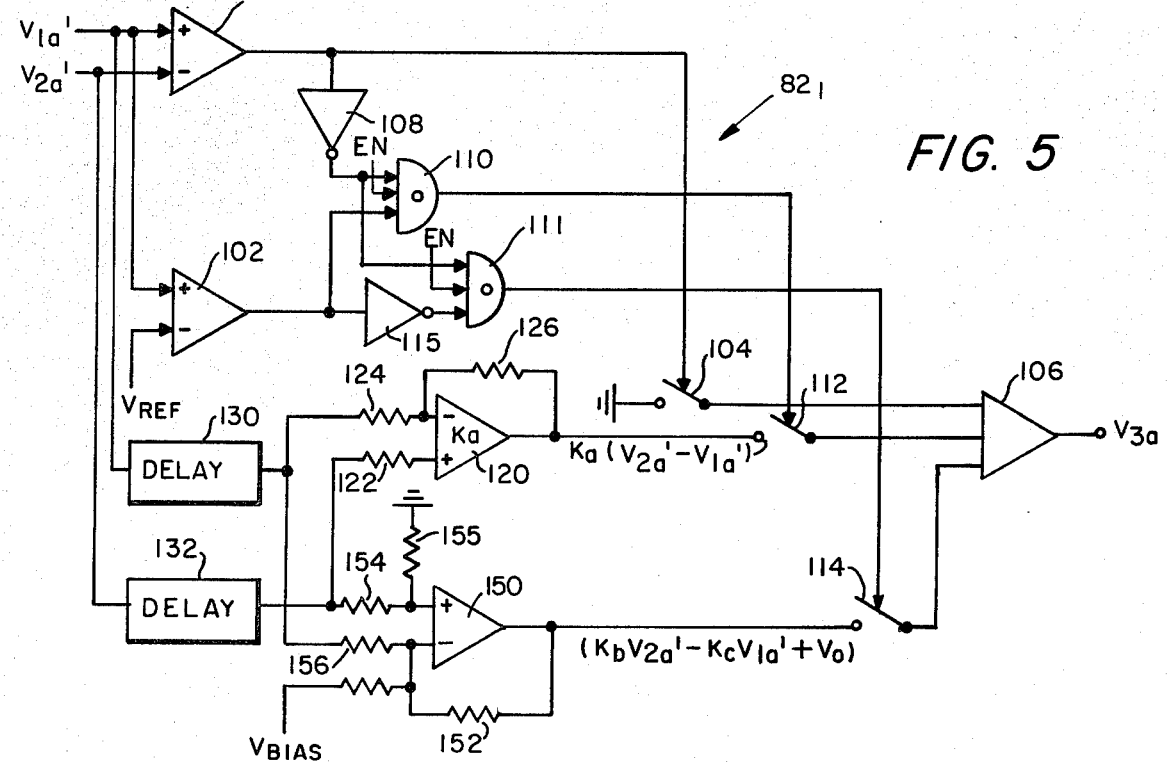
FIG. 5 is a schematic diagram of an extrapolated row outsignal generator used to produce the extrapolated signal shown by one of the curves in FIG. 4.
Figure 6:
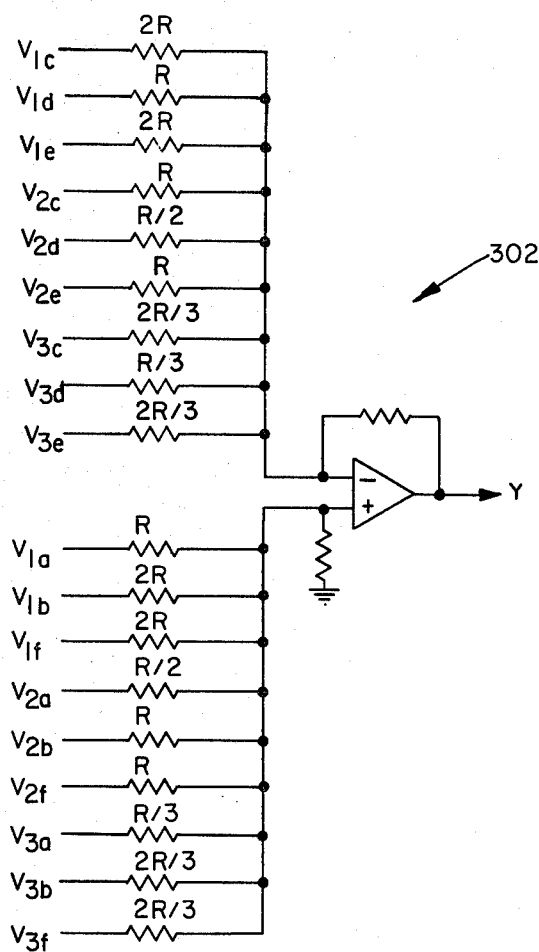
FIG. 6 is a schematic diagram of a resistor network used in the system of FIG. 1 for combining the signals produced by the row output signal generator and extrapolated row output signal generator to produce signals representative of the location of an impingement detected by the radiographic camera system of FIG. 1.
Figure 6:
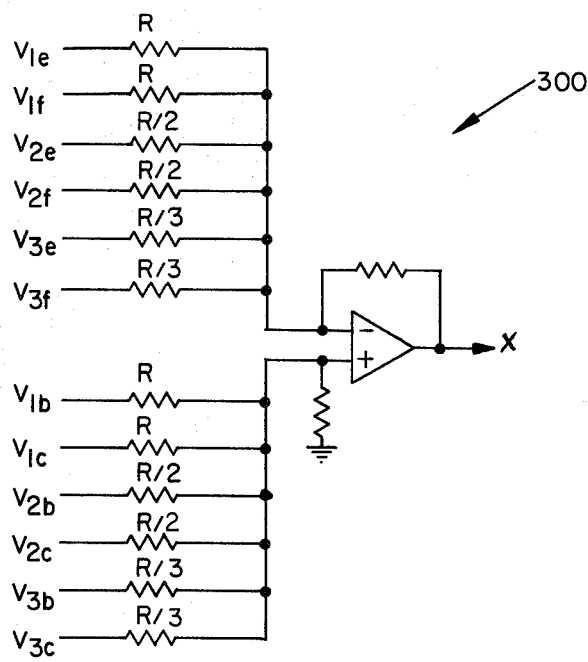

Referring now to FIG. 5, extrapolated row signal output generator $82_1$ is shown to include a pair of comparators 100, 102 connected as shown to signals $V_{1a'}$, $V_{2a'}$. Comparator 100 produces a "high" or logic 1 signal if the signal $V_{1a'}>V_{2a'}$, otherwise the output of such comparator is "low" or logic 0. The output of comparator 100 provides the control signal for an electronic switch 104 such that, when comparator 100 produces a logic 1 signal, switch 104 closes coupling ground potential (i.e., zero volts) to summing amplifier 106. The signal produced by comparator 100 is also fed, via inverter 108 through an AND gates 110, 111 to switches 112 and 114, as shown. Also fed to AND gates 110, 111 in line EN. It is noted that, when the logic 1 signal is produced by comparator 100, a logic 0 signal is produced by inverter 108 so that a corresponding logic 0 signal is produced by AND gate 110, 111 to open circuit gates 112, 114. It follows, then, that if $V_{1a'}>V_{2a'}$ the signal $V_{3a}$ produced by summing amplifier 106 is zero volts.

If the signal $V_{2a'}>V_{1a'}$ switch 104 opens and a logic 1 signal is produced by inverter 108. A comparison is made between the voltage $V_{1a'}$ and a reference voltage $V_{ref}$ (here 0.23$V_p$ volts) in comparator 102. If $V_{1a'}>V_{ref}$, comparator 102 produces a logic 1 so that in response to a pulse on line EN AND gate 110 produces a logic 1 closing gate 112. It is noted that if this condition is true (i.e., a logic 1 is produced by comparator 102) a logic 0 is produced by inverter 115 so that a logic 0 is produced by AND gate 111 to open switch 114. Under such conditions, the signal produced at the output of amplifier 120 is fed through amplifier 106. Here the signal produced at the output of amplifier 120 is $K_a$ ($V_{2a'}-V_{1a'}$) where $K_a$ is here 0.18 and is selected by the values of resistors 122, 124, 126. It is noted that signals $V_{1a'}$ and $V_{2a'}$ are fed to amplifier 120 through delay networks 130, 132, the delays provided by such networks being substantially equal to the delay in activating or deactivating the switches 104, 112, and 114. Thus, if $V_{1a'}<V_{2a'}$ and if $V_{1a'}>V_R$, the $V_{3a}=K_a(V_{2a'}-V_{1a'})$.

Continuing then, if $V_{1a'}<V_{2a'}$ and if $V_{1a'}<V_R$, then gate 114 closes and gates 104 and 112 open so that the signal produced by amplifier 150 is coupled through amplifier 106. Thus, here the signal $V_{3a}$ is $K_bV_{2a'}-K_cV_{1a'}+V_0$) where $V_0$ is here 0.365$V_p$, $K_b$ is here 0, and $K_c$ is here 1.0, the values of $K_b$ and $K_c$ being controlled by the selection of resistors 152, 154, 156, 158 and 160 and the value of $V_o$ being controlled by the voltage $V_{Bias}$.

Referring now to FIG. 6, it is noted that the resistor network 90 (FIG. 1) includes a summing amplifier 300 to produce an output voltage X representative of the X position of the impact of the gamma ray photon on the scintillator crystal 218 and a summing amplifier 302 to produce an output voltage Y representative of the Y position of such impact. Thus, taking into consideration that the voltages produced by the rows of photodetectors disposed about the outer periphery (i.e. $V_{2a}$ through $V_{2f}$) are weighted by a factor of 2 compared to the weighting of the voltages produced by the rows of photodetectors disposed about the inner periphery (i.e. $V_{1a}$ through $Y_{1f}$) and that the extrapolated voltages produced to represent the phantom rows of photodetectors (i.e. $V_{3a}$ through $V_{3f}$) are weighted by a factor of 3, the voltage X may be represented as:

$$X = V_{1b}\cos 30° + V_{1c}\cos 30° - V_{1e}\cos 30° - Y_{1f}\cos 30° + 2V_{2b}\cos 30° + 2V_{2c}\cos 30° - 2V_{2e}\cos 30° - 2V_{2f}\cos 30° + 3V_{3b}\cos 30° + 3V_{3c}\cos 30° - 3V_{3e}\cos 30° - 3V_{3f}\cos 30°$$

and, the voltage Y may be represented as:

$$Y = V_{1a} + V_{1b}\sin 30° - V_{1c}\sin 30° - V_{1d} - V_{1e}\sin 30° + V_{1f}\sin 30° + 2V_{2a} + 2V_{2b}\sin 30° - 2V_{2c}\sin 30° - 2V_{2d} - 2V_{2e}\sin 30° + 2V_{2f}\sin 30° + 3V_{3a} + 3V_{3b}\sin 30° - 3V_{3c}\sin 30° - 3V_{3d} - 3V_{3e}\sin 30° + 3V_{3f}\sin 30°.$$

It is noted that the input resistors to the summing amplifiers 300, 302 provide the appropriate scaling, as shown.

Having described a preferred embodiment of the invention it will now be apparent to one of skill in the art that other embodiments incorporating its concept may be used. It is believed therefore that this invention should not be restricted to the disclosed embodiment but rather should be limited only by the spirit and scope of the appended claims.

What is claimed is:

1. A radiographic camera, comprising:
   (a) a scintillator;
   (b) a plurality of photodetector means disposed at different, progressively increasing, predetermined distances from a reference point on the scintillator to a distal point adjacent the outer periphery of a nominal field of view of the camera, each one of such plurality of photodetector means producing a position signal representative of the distance between a point of impingement of radiation on the scintillator and such one of the photodetector means;
   (c) means, responsive to the position signals, for producing an extrapolated correction signal representative of the distance between the point of impingement and a point further than the distal point and beyond the nominal field of view of the camera; and
   (d) means, responsive to the position signals and the correction signal, for producing a pair of location signals indicative of the position of the point of impingement relative to the reference point.

2. The radiographic camera recited in claim 1 where in each one of the plurality of photodetector means includes a row of photodetectors and means for summing electrical signals produced by each one of the photodetectors in response to the impingement of the radiation on the scintillator.

3. The radiographic camera recited in claim 2 wherein the location signal producing means includes a weighting network for scaling the position signals and the correction signal.

4. A radiographic camera, comprising:
   (a) an array of photodetectors arranged in a plurality of sets of rows, the rows of photodetectors in each of such sets of rows being at successively increasing distances from a central region of the array;
   (b) means coupled to each one of the rows of photodetectors for producing an electrical signal representative of the distance between a point of light detected by the photodetectors in such row thereof and such row of photodetectors;
   (c) means, responsive to the electrical signals produced by the rows of photodetectors in each one of the sets thereof for producing an extrapolated electrical signal associated with each one of the sets thereof representative of the distance from the point of light to a row of points disposed beyond the distal one of the rows of photodetectors in such set thereof;
   (d) means, responsive to the electrical signal produced by the rows of photodetectors in each of the sets thereof and to the produced extrapolated electrical signals, for providing electrical signals indicative of the position of the point of light.

* * * * *

UNITED STATES PATENT OFFICE
CERTIFICATE OF CORRECTION

Patent No. 4,434,369                  Dated February 28, 1984

Inventor(s)  Israel Metal

It is certified that error appears in the above-identified patent and that said Letters Patent are hereby corrected as shown below:

On Cover Sheet, Item [73] Assignee:  Change "Raytheon Company, Lexington, Mass." to --The Machlett Laboratories, Incorporated, Stamford, Conn. ---.

Signed and Sealed this

Sixth Day of November 1984

[SEAL]

*Attest:*

*Attesting Officer*

GERALD J. MOSSINGHOFF

*Commissioner of Patents and Trademarks*

UNITED STATES PATENT OFFICE
CERTIFICATE OF CORRECTION

Patent No. 4,434,369            Dated February 28, 1984

Inventor(s)    Israel Metal

It is certified that error appears in the above-identified patent and that said Letters Patent are hereby corrected as shown below:

Column 1, Line 47:  Change "a" second occurrence to --the--;

Column 3, Line 16:  Change "18" to --218--;

Column 5, Line 6:   Change "$V_{2f}$ and $V_{1f}$" to --$V_{2f'}$ and $V_{1f'}$--;

Line 8:   Change "$52_{2f}$ and $52_{1f}$" to --$52_{2f'}$ and $52_{1f'}$--;

Line 10:  Change "$V_{1f}$ and $V_{2f}$" to --$V_{1f'}$ and $V_{2f'}$--;

Line 64:  Change "$V_{3f}$, $V_{2f}$" to --$V_{3f'}$, $V_{2f'}$--;

Line 67:  Change "$V_{1f}$, $V_{2f}$" to --$V_{1f'}$, $V_{2f'}$--;

Line 68:  Change "$V_{3f}$" to --$V_{3f'}$--;

UNITED STATES PATENT OFFICE
CERTIFICATE OF CORRECTION

Patent No. 4,434,369    Dated February 28, 1984

Inventor(s) Israel Metal

It is certified that error appears in the above-identified patent and that said Letters Patent are hereby corrected as shown below:

Column 6, Line 1: Change "$V_{3f}$" to --$V_{3f'}$--;

Line 4: Change "$V_{3f}$" to --$V_{3f'}$--;

Line 5: Change "$V_{1f}, V_{2f}$" to --$V_{1f'}, V_{2f'}$--; and

Line 30: Change "in" to --is--.

*Signed and Sealed this*

*Twenty-fifth* Day of *December 1984*

[SEAL]

Attest:

Attesting Officer

GERALD J. MOSSINGHOFF

*Commissioner of Patents and Trademarks*